United States Patent [19]

Lossnitzer et al.

[11] Patent Number: 5,047,235

[45] Date of Patent: Sep. 10, 1991

[54] PHARMACEUTICAL PREPARATIONS HAVING AN ANTIHYPERTENSIVE AND CARDIOPROTECTIVE EFFECT

[75] Inventors: Klaus Lossnitzer, Bad Kissingen; Karl-Friedrich Ober, Darmstadt; Gerhard Giebenhain, Muhltal; Gerhard Zeiss, Gross-Gerau; Karl-Dieter Volger, Bickenbach, all of Fed. Rep. of Germany

[73] Assignee: Rohm-Pharma GmbH, Weiterstadt, Fed. Rep. of Germany

[21] Appl. No.: 251,921

[22] Filed: Sep. 30, 1988

Related U.S. Application Data

[63] Continuation of Ser. No. 860,235, May 6, 1986, abandoned.

[30] Foreign Application Priority Data

May 17, 1985 [DE] Fed. Rep. of Germany ....... 3517820

[51] Int. Cl.$^5$ ..................... A61K 31/79; A61K 31/54
[52] U.S. Cl. .................................... 424/80; 514/223.5; 514/649; 514/249; 424/78
[58] Field of Search ................. 424/80, 78; 514/223.5, 514/649, 249, 253

[56] References Cited

U.S. PATENT DOCUMENTS

| | | | |
|---|---|---|---|
| 4,157,394 | 6/1979 | Fleckenstein et al. | 424/251 |
| 4,444,769 | 4/1984 | Blume et al. | 424/246 |
| 4,526,777 | 7/1985 | Blume et al. | 424/246 |

OTHER PUBLICATIONS

Herz-Kreislauf-3/1980 pp. 126-131 Lossnitzer et al.
C&EN, (1982), "New Drugs for Combating Heart Disease", Howard J. Sanders.
Drugs, (1983), vol. 25, "Beta-Blockers and Calcium Antagonists", F. R. Buehler, et al.
Synergistiche Blutdrucksenkung, (1988), "Verapamil-Diuretika-Kombination", Professor Dr. Rer. Nat. Dr. Med. Ernst Mutschler.
Arch Intern Med, (1989), vol. 149, pp. 125-128, "Hydrochlorothiazide is not Additive to Verapamil in Treating Essential Hypertension", J. P. Nicholson et al.
F. R. Buhler, et al, Drugs, 25(Suppl.2):50-57 1983.
Von K. Greeff, Arzeim-Forsch/Drug Res., 29(I) Nr. 4., 1979, p. 619.
L. Joubert, et al., Canadian Med. Assoc. J., 99(2), 57-63, 1968.
C&E News, Jul. 12, 1982.
Ullmanns Encyoclopedia der technischen Chemie, p. 583, (1970).
J. L. Kalliomaki et al., Current Therapeutic Research, 11(6), 1969.
Autorenreferate, p. 86 (1983).
Unlisted Drugs, Band 31, Nr. 9, Sep., 1979, Seite 135.
Unlisted Drugs, Band 21, Nr. 9, Sep., 1969, Seite 142.
Unlisted Drugs, Band 35, Nr. 5, May 1983, Seite 76.
Rote Liste, 1982, Editio Cantor, Nr. 35055, "Dytide H", Nr. 35056, Esiteren, Nr. 35058, Triamthiazid Henning and Nr. 35059, Tri-Thiazid Stada.

Primary Examiner—Peter F. Kulkosky
Attorney, Agent, or Firm—Oblon, Spivak, McClelland, Maier & Neustadt

[57] ABSTRACT

A pharmaceutical preparation, which has an anti-hypertensive and cardio-protective effect, which coprises a pharmaceutically effective amount of a combination of α-isopropyl-α-[(N-methyl-N-homoveratryl)-γ-aminopropyl]-3,4-dimethoxyphenyl-acetonitrile in the form of pharmacologically acceptable acid addition salt, 2,4,7-triamino-6-phenyl-pteridine and 6-chloro-3,4-dihydro-7-sulfamoyl-2H-1,2,4-benzothiadiazine-1,1-dioxide as acitve ingredients, in combination with a carrier and auxiliary materials in single dosage form.

10 Claims, No Drawings

PHARMACEUTICAL PREPARATIONS HAVING AN ANTIHYPERTENSIVE AND CARDIOPROTECTIVE EFFECT

This application is a continuation of application Ser. No. 06/860,235 filed on May 6, 1986, now abandoned.

BACKGROUND OF THE INVENTION

1. Field of the Invention

The present invention relates to a pharmaceutical preparation, which has an antihypertensive and cardioprotective effect formed from the combination of a calcium antagonist, the potassium saver—Triamterene—and the diuretic drug—Hydrochlorothiazide.

2. Discussion of the Prior Art

Pharmaceutical preparations having cardio-protective effects and containing calcium antagonistic active agents, in particular Verapamil, which is combined wtih Triamterene, are known as disclosed in U.S. Pat. No. 4,157,394. These preparations have interesting properties, i.e. the active components have a greater effect.

From the viewpoint of the results desired in the diuretic therapy, a need continues to exist for a preparation having explicit diuretic and, at the same time, cardio-protective properties. However, there are a number of reasons why one skilled in the art would not expect this objective to be realistic, especially if the active agents—Verapamil and Triamterene—are used in such therapy:

Verapamil lowers the blood pressure. The usual dosage administered is relatively high (240 mg per day). Therefore, the daily dosages are usually divided up or administered in a slow form (cf. "red list"). Triamterene is also added primarily in combination with the diuretic agent—Hydrochlorothiazide. The usual dosage that is recommended to lower the blood pressure ranges from 1-2 tablets per day, with the dosage being—50 mg Triamterene plus 25 mg Hydrochlorothiazide per tablet. However, a need continues to exist for a drug formulation which exhibits improved antihypertensive and cardio-protective properties.

SUMMARY OF THE INVENTION

Accordingly, one objective of the present invention is to provide a therapeutic formulation of improved cardio-protective properties and antihypertensive properties.

Briefly, this object and other objects of the present invention as hereinafter will become more readily apparent can be attained by an antihypertensive and cardio-protective effective amount of a combination of the compound, α-isopropyl-α-[(N-methyl-N-homoveratryl)-γ-aminopropyl]-3,4-dimethoxyphenyl-acetonitrile, in the form of its pharmacologically acceptable acid addition salts, especially the hydrochloride ("Verapamil"), 2,4,7-triamino-6-phenylpteridine ("Triamterene"), and 6-chloro-3,4-dihydro-7-sulfamoyl-2H-1,2,4-benzothiadiazine-1,1-dioxide ("Hydrochlorothiazide") as the active ingredients.

DETAILED DESCRIPTION OF THE PREFERRED EMBODIMENTS

The pharmacological acceptable acid addition salts of the acetonitrile derivative of the present composition include the salts of the derivative with d-tartaric acid, maleic acid, fumaric acid, succinic acid, citric acid, cinnamic acid, salicyclic acid, adipic acid, acetic acid, propionic acid, p-aminobenzoic acid, methanesulfonic acid, sulfuric acid, phosphoric acid, and particularly hydrochloric acid and lactic acid.

In the preferred embodiment of the present composition, the three active agents are combined in unit dosage form, preferably as a tablet, specifically in a weight ratio (approximately to exact) of 16 weight parts Verapamil:5 weight parts Triamterene:2.5 weight parts Hydrochlorothiazide, particularly preferably in a ratio of 160 mg:50 mg:25 mg. This formation makes available, in the form of a tablet, a daily dosage of 160 mg Verapamil, 50 mg Triamterene, and 25 mg Hydrochlorothiazide. This also makes it possible to administer the drug in capsule or dragee form. The pharmaceutical preparation of the invention can be administered enterally. However, oral administration, is preferred. The preparation can further comprise the usual additives and carrier materials.

The preferred embodiment of the preparation of the present invention is a solid which is suitable for oral administration, particularly tablets. Pharmaceutically indifferent solids includes, for example, mannite, lactose, organic or inorganic calcium salts, and the like as carrier materials.

The binder component of the present composition includes the likes of polyvinyl pyrrolidone, gelatin, and cellulose derivatives. Further additives include tablet-rupturing agents such as starch and alginic acid; lubricants such as stearic acid and the salts thereof and inorganic flow agents such as talc and colloidal silicic acid, as well as agents which adjust or change the taste of the composition.

The active agents can be mixed with the auxiliaries in the usual manner and granulated under wet or dry conditions. According to the kind of additive used, a powder, which can be made directly into tablets can also be obtained by simple mixing. The granulate or powder can be filled directly into capsules or can be pressed in the usual way to form tabletcores.

The formulation of the present invention provides a process for treating high blood pressure. According to the invention, a tablet, containing 160 mg Verapamil, 50 mg Triamterene and 25 mg Hydrochlorothiazide, is administered as a daily dosage.

According to the invention, the combination of ingredients of the present composition has a therapeutic effect that extends beyond the effect of the individual components. It should be emphasized that this effect can be evoked with a relatively small single dosage of the individual components, namely 160 mg Verapamil, 50 mg Triamterene and 25 mg Hydrochlorothiazide.

Having generally described this invention, a further understanding can be obtained by reference to certain specific examples which are provided herein for purposes of illustration only and are not intended to be limiting unless otherwise specified.

The tablets, which contain the active agent combination in a one-a-day dosage, can be prepared as follows:

The tablets can be expediently prepared in several stages:

A. Preparation of a 100 kg Verapamil granulate (60.4% Verapamil hydrochloride):

| | |
|---|---|
| Verapamil hydrochloride | 60.38 kg |
| Aerosil ® pyrogen silicic acid | 0.51 kg |
| microcrystalline cellulose (Avicel ® PH 102) | 19.10 kg |
| calcium-carboxymethylcellulose | 5.00 kg |

| -continued | |
|---|---|
| (Emcompress ®) auxiliaries for making tablets of dicalcium phosphate | 10.00 kg |
| magnesium stearate | 1.51 kg |
| talcum | 3.50 kg |

Verapamil hydrochloride, Aerosil ®, Avicel ® PH 102, calcium carboxymethylcelulose, and Emcompress ® and talcum are mixed in a mixer (FKM 130 Lodi-mixer) for 5 minutes with a cutter cross and, sieved through 0.9 mm mesh. Magnesium stearate is then added. The ingredients are mixed with a cutter cross for another 10 minutes. Then it is pressed into a solid form in a compactor.

With the roller setting at 9, the material feed screw at a setting of 8-9, the mass is compressed under a roller pressure of 70-80 kN on the Hutt compactor. During this proces the temperature of the pressed mass is approximately 35° C. Then, the mass is granulated with the granulating sieve, having a mesh size of 0.9 mm. In the flow test the granulate demonstrates relatively good flow properties: 4-8 sec. Passage test 7-8 mm. Bulk density 6.3-6.9 g/ml. Verapamil content 60.38%, 97.2-10.5% of the desired value.

B. Preparation of a mass for Triamterene-Hydrochloro-thiazide-tablets

The following description provides a receipe for the preparation of a 50 kg batch of tablets:

| | |
|---|---|
| Triamterene | 12.500 kg |
| Hydrochlorothiazide | 6.250 kg |
| calcium carbonate | 1.860 kg |
| pyrogen silicic acid (Aerosil ®) | 0.410 kg |
| maize starch | 2.660 kg |
| lactose K | 2.160 kg |
| lactose granulate | 13.200 kg |
| polyvinyl pyrrolidone (average molecular weight 25,000) | 0.390 kg |
| magnesium sterate | 0.550 kg |
| microcrystalline cellulose | 4.820 kg |
| carboxymethyl starch | 1.000 kg |
| talcum | 4.200 kg |

C. Preparation of a Triamterene-Hydrochlorothiazide-Verapamil tablet (ratio 50 mg:25 mg:160 mg)

The Verapamil granulate prepared as described in section A, and the tablet mass, prepared as described in Section B, are sieved in the indicated ratios and mixed in a Rhon wheel mixer. The mixed material was beveled on a circular tablet press, having a tool diameter of 10 mm, and pressed into tablets without a breaking notch at 35 revolutions per minute and a press pressure of 8-10 kN. By this procedure, tablets with a weight of 465 mg were obtained.

The effectiveness of the active agent combination of the invention, originates from the following double blank study.

A total of 9 treatment groups with 24 patients per group were formed. The patients were treated for hypertension. After a two-week placebo phase they had a systolic blood pressure of 160-180 mm Hg and a diastolic blood pressure of 95-120 mm Hg. After the placebo phase the patients were given over a three-week period, once in the morning, in random order either 1. placebo
2. 80 mg Verapamil-hydrochloride (V)
3. 160 mg Verapamil-hydrochloride (V)
4. 12.5 mg Hydrochlorothiazide (HCT) and 25 mg Triamterene (TA)
5. 25 mg Hydrochlorothiazide (HCT) and 50 mg Triamterene (TA)
6. 12.5 mg HCT, 25 mg TA, 80 mg V
7. 12.5 mg HCT, 25 mg TA, 160 mg V
8. 25 mg HCT, 50 mg TA, 80 mg V
9. 25 mg HCT, 50 mg TA, 160 mg V In the morning, before administering the drug, the systolic and diastolic blood pressure of each patient was measured after each patient had laid down for 3 minutes and after they had stood up for 1 minute.

The active agents were administered in the form of tablets prepared as described above.

The table below shows the antihypertension effect of the Triamterene-Hydrochlorothiazide-Verapamil combination for a single dosage. The combination—25 mg HCT, 50 mg TA, and 160 mg V—had the most favorable effect. (Dytide H stands for the combination of 25 mg HCT plus 50 mg TA.)

| | Mean Change in Blood Pressure in Various Treatment Groups | | | | | |
|---|---|---|---|---|---|---|
| | measurement in the (sys./diast.) prone position | | | measurement in the (syst./diast.) standing position | | |
| Treatment Group | end of placebo phase (mmHg) | end of treatment (mmHg) | % change (%) | end of placebo phase (mmHg) | end of treatment (mmHg) | % change (%) |
| Placebo | 174.6/101.4 | 169.8/99.2 | −2.7/−2.2 | 172.8/100.0 | 169.8/100.6 | −1.7/+0.6 |
| Verapamil 80 mg | 169.0/100.2 | 164.2/98.8 | −2.9/−1.3 | 171.0/100.0 | 166.5/99.7 | −2.6/−0.3 |
| Verapamil 160 mg | 175.3/104.7 | 159.7/97.5 | −8.9/−6.9 | 177.3/105.0 | 162.7/97.0 | −8.3/−7.6 |
| ½Dytide H | 175.6/105.4 | 176.8/102.8 | +0.7/−2.5 | 177.6/106.0 | 175.8/102.4 | −1.0/−3.4 |
| 1/1 Dytide H | 171.4/103.2 | 165.6/100.0 | −3.4/−3.2 | 170.6/103.6 | 165.8/99.2 | −2.8/−4.7 |
| ½Dytide H + Verapamil 80 mg | 172.8/100.5 | 155.5/91.8 | −10.0/−8.6 | 172.3/100.7 | 156.0/93.3 | −9.5/−7.3 |
| 1/1 Dytide H + Verapamil 160 | 175.2/104.5 | 155.3/88.5 | −11.3/−15.3 | 173.8/103.7 | 157.5/90.3 | −9.4/−12.9 |
| 1/1 Dytide H + Verapamil 80 mg | 176.0/104.7 | 158.0/94.5 | −10.2/−9.7 | 174.5/105/3 | 156.5/94./2 | −10.3/−10.6 |
| 1/1 Dytide H + Verapamil 160 mg | 174.5/105.7 | 151.7/89.7 | −13.1/−15.1 | 172.0/103.0 | 152.0/90.7 | −11.6/−12.0 |

Having now fully described the invention, it will be apparent to one of ordinary skill in the art that many changes and modifications can be made thereto without departing from the spirit or scope of the invention as set forth herein.

What is claimed as new and desired to be secured by letters patent of the United States is:

1. A composition, comprising:
   (i) α-isopropyl-α-[(N-methyl-N-homoveratryl)-γ-aminopropyl]-3,4-dimethoxyphenyl-acetonitrile, or a pharmacologically acceptable salt thereof;

(ii) 2,4,7-triamino-6-phenylpteridine, or a pharmacologically acceptable salt thereof; and (iii) 6-chloro-3,4-dihydro-7-sulfamoyl-2H-1,2,4-benzothiadiazine-1,1-dioxide, or a pharmacologically acceptable salt thereof;

wherein (i), (ii) and (iii) are present together in a weight ratio of about 16:5:2.5.

2. The composition of claim 1, wherein said α-isopropyl-α-[(N-methyl)-N-homoveratryl)-γaminopropyl]-3,4-dimethoxyphenyl-acetonitrile is present in the form of its hydrochloride salt.

3. The composition of claim 1, wherein said α-isopropyl-α-[(N-methyl-N-homoveratryl)-γ-aminopropyl]-3,4-dimethoxyphenylacetonitrile is present in the form of its acid addition salt with d-tartaric acid, maleic acid, fumaric acid, succinic acid, citric acid, cinnamic acid, salicyclic acid, adipic acid, acetic acid, propionic acid, p-aminobenzoic acid, methane sulfonic acid, sulfuric acid, phosphoric acid, hydrochloric acid or lactic acid.

4. A pharmaceutical preparation which has an antihypertensive and cardio-protective effect, which comprises:

a pharmaceutically effective amount of a combination of α-isopropyl-α-[(N-methyl-N-homoveratryl)-γ-aminopropyl]-3,4-dimethoxyphenylacetonitrile in the form of a pharmacologically acceptable acid addition salt, 2,4,7-triamino-6-phenylpteridine, and 6-chloro-3,4-dihydro-7-sulfamoyl-2H-1,2,4-benzothiadiazine-1,1-dioxide as active ingredients, in combination with a carrier and auxiliary materials, wherein:

said α-isopropyl-α-[(N-methyl-N-homoveratryl)-γ-aminopropyl]-3,4-dimethoxyphenylacetonitrile in the form of a pharmacologically acceptable acid addition salt; said 2,4,7-triamino-6-phenylpteridine; and said 6-chloro-3,4-dihydro-7-sulfamoyl-2H-1,2,4-benzothiadiazine-1,1-dioxide are present in a weight ratio of about 16:5:2.5.

5. The pharmaceutical preparation of claim 4, wherein said α-isopropyl-α-[(N-methyl-N-homoveratryl)-γ-aminopropyl]-3,4-dimethoxyphenyl-acetonitrile is present in the form of its hydrochloride salt.

6. The pharmaceutical preparation of claim 4 in a form suitable for oral administration.

7. The pharmaceutical preparation of claim 4 in tablet form.

8. The pharmaceutical preparation of claim 4, wherein the combination of active ingredients comprises 160 mg Verapamil, 50 mg Triamterene, and 25 mg Hydrochlorothiazide.

9. The pharmaceutical preparation of claim 4, wherein said α-isopropyl-α-[(N-methyl-N-homoveratryl)-γ-aminopropyl-3,4-dimethoxyphenylacetonitrile is present in the form of its acid addition salt with d-tartaric acid, maleic acid, fumaric acid, succinic acid, citric acid, acetic acid, propionic acid, aminobenzoic acid, methane sulfonic acid, sulfuric acid, phosphoric acid, hydrochloride acid or lactic acid.

10. The pharmaceutical preparation of claim 4, wherein said auxiliary material is a binder selected from the group consisting of polyvinylpyrrolidone, gelatin and cellulose derivatives.

* * * * *

UNITED STATES PATENT AND TRADEMARK OFFICE
CERTIFICATE OF CORRECTION

PATENT NO. : 5,047,235

DATED : September 10, 1991

INVENTOR(S) : Klaus LOBNITZER et al

It is certified that error appears in the above-identified patent and that said Letters Patent is hereby corrected as shown below:

Title page, item, [75]

The name of the fifth listed inventor should read -- Karl-Dieter Voelger -- .

Title page, under "OTHER PUBLICATIONS"

The fourth listed publication is -- Synergistische Blutdrucksenkung --.

The tenth listed publication is -- Ullmanns Encyclopedia der technischen Chemie --.

In the abstract on line 9, "acitve" should read -- active --.

In Column 1, line 19, "wtih" should read -- with --.

UNITED STATES PATENT AND TRADEMARK OFFICE
CERTIFICATE OF CORRECTION

PATENT NO. : 5,407,235

DATED : September 10, 1991

INVENTOR(S) : Klaus LOBNITZER et al

It is certified that error appears in the above-identified patent and that said Letters Patent is hereby corrected as shown below:

In Column 3, line 9, "carboxymethylcelulose" should read -- carboxymethylcellulose --;

line 57, "sterate" should read -- stearate --.

Signed and Sealed this

Twenty-second Day of June, 1993

Attest:

MICHAEL K. KIRK

*Attesting Officer*  *Acting Commissioner of Patents and Trademarks*